United States Patent [19]
Ji et al.

[11] Patent Number: 6,120,446
[45] Date of Patent: Sep. 19, 2000

[54] DIAGNOSTIC MEDICAL ULTRASONIC IMAGING SYSTEM AND METHOD WITH ADAPTIVE GAIN

[75] Inventors: Ting-Lan Ji, San Jose; Ismayil M. Guracar, Redwood City, both of Calif.

[73] Assignee: Acuson Corporation, Mountain View, Calif.

[21] Appl. No.: 09/213,666

[22] Filed: Dec. 17, 1998

[51] Int. Cl.[7] .............................. A61B 8/00; G01N 29/04
[52] U.S. Cl. .......................... 600/437; 600/443; 73/631
[58] Field of Search .................................. 600/443, 447, 600/437; 73/631, 625–626; 367/7, 11

[56] References Cited

U.S. PATENT DOCUMENTS

| | | | |
|---|---|---|---|
| 4,433,304 | 2/1984 | Engle | 330/281 |
| 4,475,400 | 10/1984 | Flax | 73/631 |
| 4,545,251 | 10/1985 | Uchida et al. | 73/631 |
| 4,662,380 | 5/1987 | Riley | 128/660 |
| 4,785,818 | 11/1988 | Hardin | 600/443 |
| 4,852,576 | 8/1989 | Inbar et al. | 128/660.6 |
| 5,313,948 | 5/1994 | Murashita et al. | 128/662.02 |
| 5,479,926 | 1/1996 | Ustuner et al. | 128/660.04 |
| 5,482,045 | 1/1996 | Rust et al. | 128/661.01 |
| 5,501,221 | 3/1996 | Foster et al. | 128/660.06 |
| 5,579,768 | 12/1996 | Klesenski | 128/660.06 |
| 5,594,807 | 1/1997 | Liu | 382/128 |
| 5,799,111 | 8/1998 | Guissin | 382/254 |

FOREIGN PATENT DOCUMENTS 0 843 181 A1  5/1998  European Pat. Off. .

*Primary Examiner*—Francis J. Jaworski
*Attorney, Agent, or Firm*—Brinks Hofer Gilson & Lione

[57] ABSTRACT

A diagnostic medical ultrasonic imaging system includes a gain processor that varies the receive signal path gain as a function of the signal to noise ratio of the echo signal. Background noise is either acquired or modeled in real time using currently prevailing imaging parameters, and acquired echo signals are compared with the acquired or modeled background noise values. The receive gain is controlled as a function of this comparison to improve the signal-to-noise ratio, and to reduce or prevent the amplification of echo signals that are not greater than the background noise level.

34 Claims, 7 Drawing Sheets

DIAGNOSTIC MEDICAL ULTRASONIC IMAGING SYSTEM AND METHOD WITH ADAPTIVE GAIN

BACKGROUND

The present invention relates to ultrasonic imaging systems, and in particular to diagnostic medical ultrasonic imaging systems having adaptive gain in the receive signal path.

It is well known in medical ultrasound imaging that as ultrasonic waves penetrate into a patient's body and return after reflection they are continually attenuated. To compensate for this attenuation, ultrasound imaging systems have traditionally applied a depth dependent gain to the returning echoes. As ultrasonic signals return from increasing depth the applied gain is increased accordingly. This type of gain compensation is generally called depth gain compensation (DGC), or time gain compensation (TGC), because the depth of an echo corresponds to the time taken for the echo to reach a reflecting object and return to the transducer. In this specification, the term depth gain compensation (DGC) will be used to represent this pre-determined range-varying gain function, which preferably does not include the additional gain applied by the user through the commonly called DGC potentiometers (or TGC potentiometers).

Several U.S. patents discuss how to implement DGC, how to predetermine the DGC curve for the selected application, and how to design the system to adjust the DGC curve automatically (see U.S. Pat. No. 4,662,380, U.S. Pat. No. 4,852,576, U.S. Pat. No. 5,313,948, U.S. Pat. No. 5,501,221, U.S. Pat. No. 5,482,045, and U.S. Pat. No. 5,579,768). The common problem with these DGC methods is that as the returning ultrasonic signal is amplified by the DGC, the background noise (the combination of front-end noise and system noise) is also amplified by the same DGC. Since the echo signals from tissue objects decrease in amplitude with depth, but the background noise does not, the output signal-to-noise ratio (SNR) of the image decreases with increasing depth. The penetration limit is often primarily determined by this ratio.

In European patent EP-0843181A1 titled "Variable Compression of Ultrasonic Image Data with Depth and Lateral Scan Dimensions", a means for automatically varying the displayed dynamic range and noise rejection level throughout the image is described.

Thus, a need presently exists for systems that improve the signal-to-noise ratio of medical diagnostic imaging signals at increased depths.

SUMMARY

By way of introduction, the preferred embodiments described below obtain a plurality of reference values which vary as a function of real time background noise at multiple locations within a frame. These reference values may be obtained from acquired background noise in the absence of transmitted ultrasonic energy, or by modeling the background noise as a function of the currently prevailing imaging parameters of the ultrasonic imaging system. Ultrasonic echo signals are compared with respective ones of these reference values, and a gain function is selected in response to the comparison and applied to the ultrasonic echo signals. In this way, the applied gain function can be varied depending upon the SNR of the echo signals, and the amplification of noise can thereby be reduced.

The present invention is defined by the following claims, and nothing in this section should be taken as a limitation on those claims.

DETAILED DESCRIPTION OF THE PRESENTLY PREFERRED EMBODIMENTS

The following detailed description will begin with a general discussion of selected embodiments of this invention, and will then turn to a detailed description of two specific examples.

General Discussion

As discussed in greater detail below, the following preferred embodiments provide a back end gain processor for medical diagnostic imaging systems. The back end gain processor is designed to apply different gain values to an ultrasonic echo signal (such as for example a B-mode signal) according to the echo signal strength. In the first embodiment described below the gain processor stores one frame of magnitude-detected, log-compressed image signals that have been acquired using the currently prevailing B-mode imaging parameters without transmitting ultrasonic energy. These image signals are stored as a reference image for background noise, and they represent an actual measurement of currently prevailing background noise for the given imaging parameters. A threshold image is derived based on this acquired noise reference image. Then, all subsequent normal image frames (such as for example B-mode image frames) are compared to the threshold image on a pixel-by-pixel basis.

Figure 2:
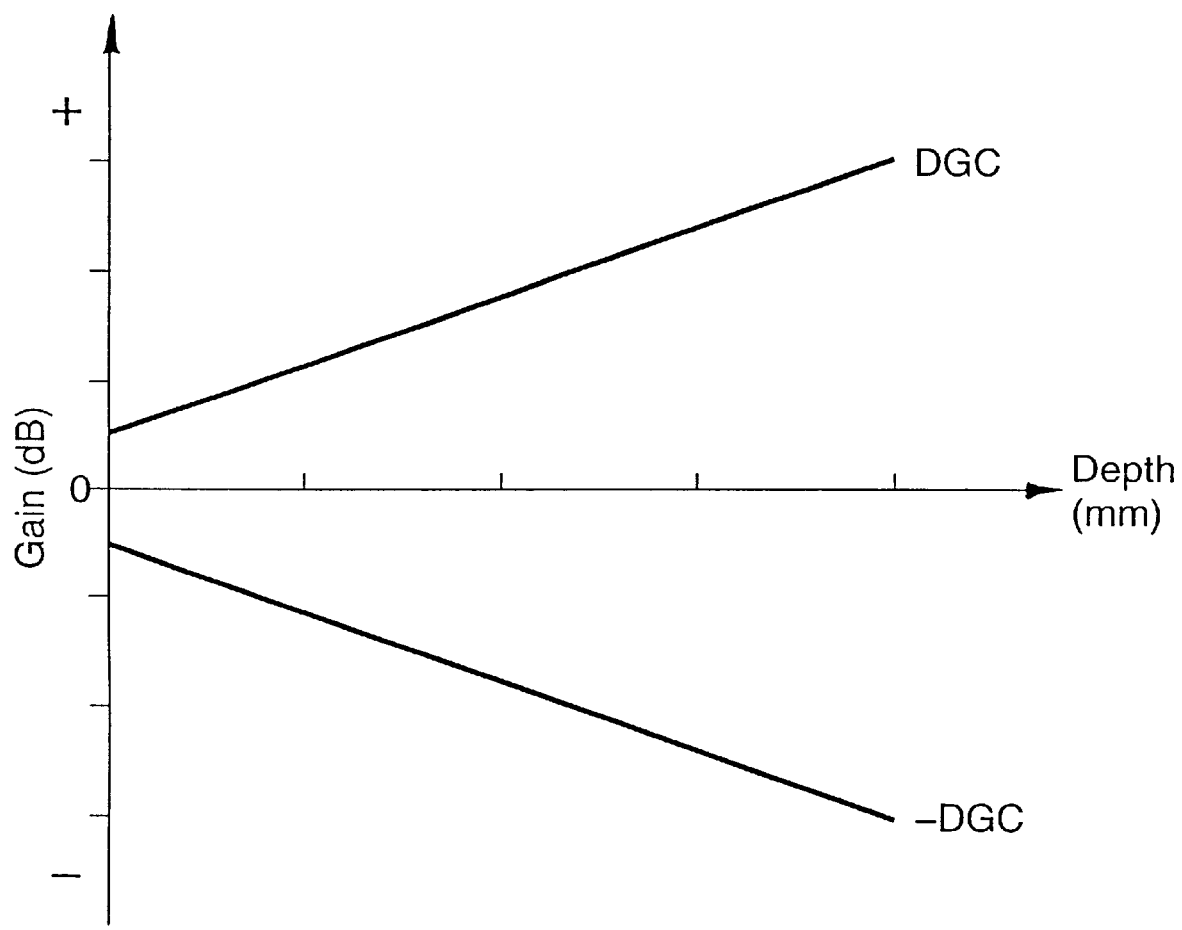
FIG. 2 is a graph showing a DGC gain function and an inverse DGC gain function used in the embodiment of FIG. 1.

If a B-mode image value is greater than the threshold at that pixel, it is classified as signal and no action is taken; if the B-mode image value is smaller than the threshold at that pixel, it is classified as noise and a inverse DGC function, or a negative DGC function in log domain, is applied. In other words, the total system gain applied to each pixel of the image depends on the SNR at that point. By way of example, a DGC gain function and the associated inverse DGC gain function are shown in FIG. 2. In the above process, the background noise frame needs to be acquired only once, until the B-mode imaging settings as adjusted by the user result in a background noise change (e.g., transmit focus change, frequency change, etc.). Then the background noise image will be re-acquired and the above process will repeat to determine the new threshold image.

To be more specific, assume $I_n(x, y)$ represents the acquired background noise image. This noise image is then filtered by a low-pass filter $h(x, y)$ (e.g., a boxcar filter) to obtain a smoothed version of $I_n(x, y)$:

$$I_n^{sm}(x, y)=I_n(x, y)*h(x, y).$$

The threshold image is derived by $$I_T(x, y)=I_n^{sm}(x, y)+k\sigma_n,$$

where * denotes convolution, and $\sigma_n$ is the standard deviation of $\{I_n(X, Y) - I_n^{sm}(x, y)\}$. The constant k is an adjustable scale factor and its preferred value is 3 in this embodiment.

Let $I_i(x, y)$ be the magnitude-detected and log-compressed B-mode signal. The output $I_o(x, y)$ is formed as follows:

$$I_o(x, y)=I_i(x, y)$$

If $I_i(x, y) > I_T(x, y)$, $$I_o(x, y)=I_i(x, y)+G_I(r)$$

If $I_i(x, y) < I_T(x, y)$, where $G_I(r)=-DGC(r)$ is the inverse DGC function. In order to achieve a smooth transition between the two very different DGC gain functions, the preferred approach is to define a weighting factor αx, which is a continuous function of $I_i(x, y)$ and has a sigmoidal shape with its transition slope being an adjustable parameter, and thus $$I_o(x, y)=I_i(x, y)-(1-\alpha)DGC(r).$$

Figure 6:
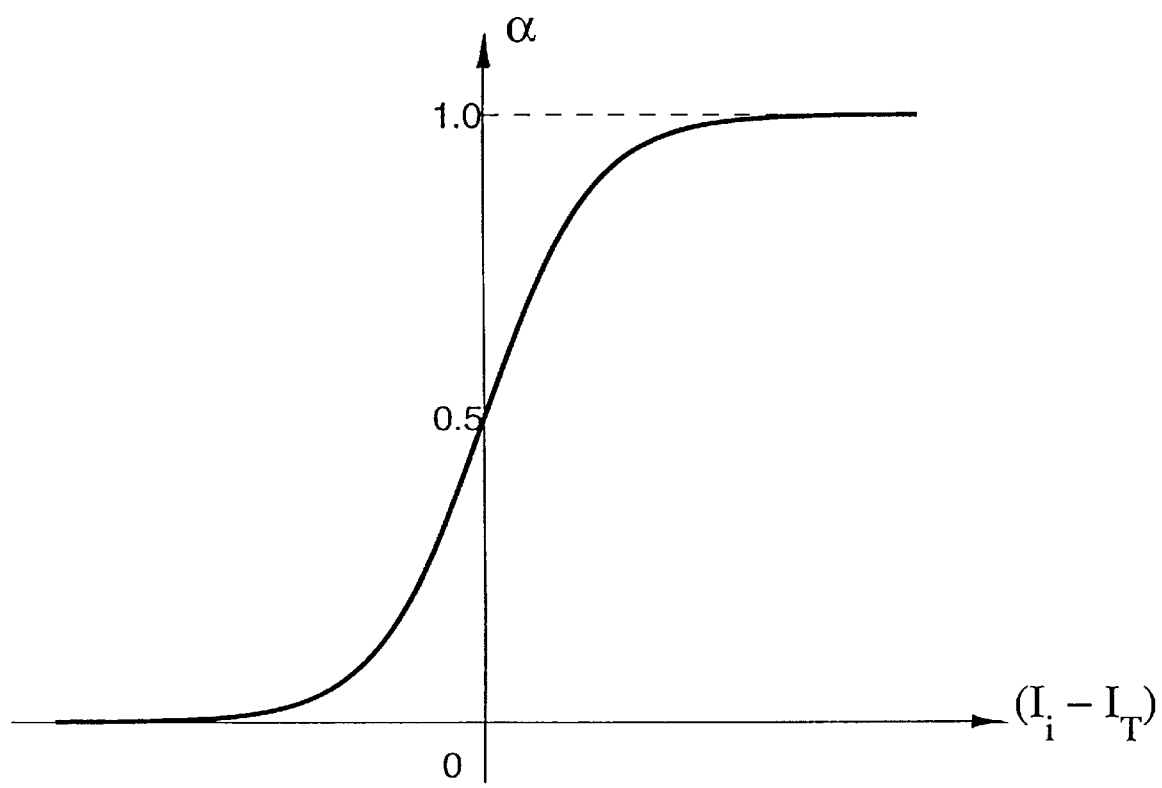
FIG. 6 is a graph of a weighting function.

An example of such weighting function α is shown in FIG. 6.

The B-mode signal can be obtained either from fundamental imaging or harmonic imaging, as long as the background noise image is also obtained from the same B-mode imaging modality. In the foregoing description, the inverse DGC gain is assumed to be applied to the magnitude-detected and log-compressed B-mode signal. This should be treated as one example of the embodiments of this invention, rather than as a limitation. For example, different gains can also be applied to the detected B-mode signal and noise before log-compression. In addition, we may or may not choose to include any depth-independent gain $G_o$ (e.g., the master gain adjusted by the user) into this scheme. In one alternative embodiment we may choose:

$$I_o(x, y)=I_i(x, y)+(1-\alpha)(G_o-DGC(r),$$

so that the depth-independent gain $G_o$ primarily applies to B-mode signals which are greater than the threshold $I_T(x, y)$.

In another embodiment, we may choose not to include depth-independent gain $G_o$ into the SNR dependent gain scheme:

$$I_o(x, y)=I_i(x, y)-(1-\alpha)DGC(r)+G_o,$$

so that the background noise is subject to the depth-independent gain only.

In another embodiment, we may choose to include a part of $G_o$ into the SNR dependent gain control:

$$I_o(x, y)=I_i(x, y)+(1-\alpha)(\beta G_o-DGC\ (r))+(1-\beta)G_o(0<\beta<1),$$

so that only a part of depth-independent gain is applied to the background noise.

In the preferred embodiment, the user gain controlled by the DGC potentiometers is not included in this SNR dependent gain scheme, and maintains its normal behavior.

Specific Examples

Figure 1:
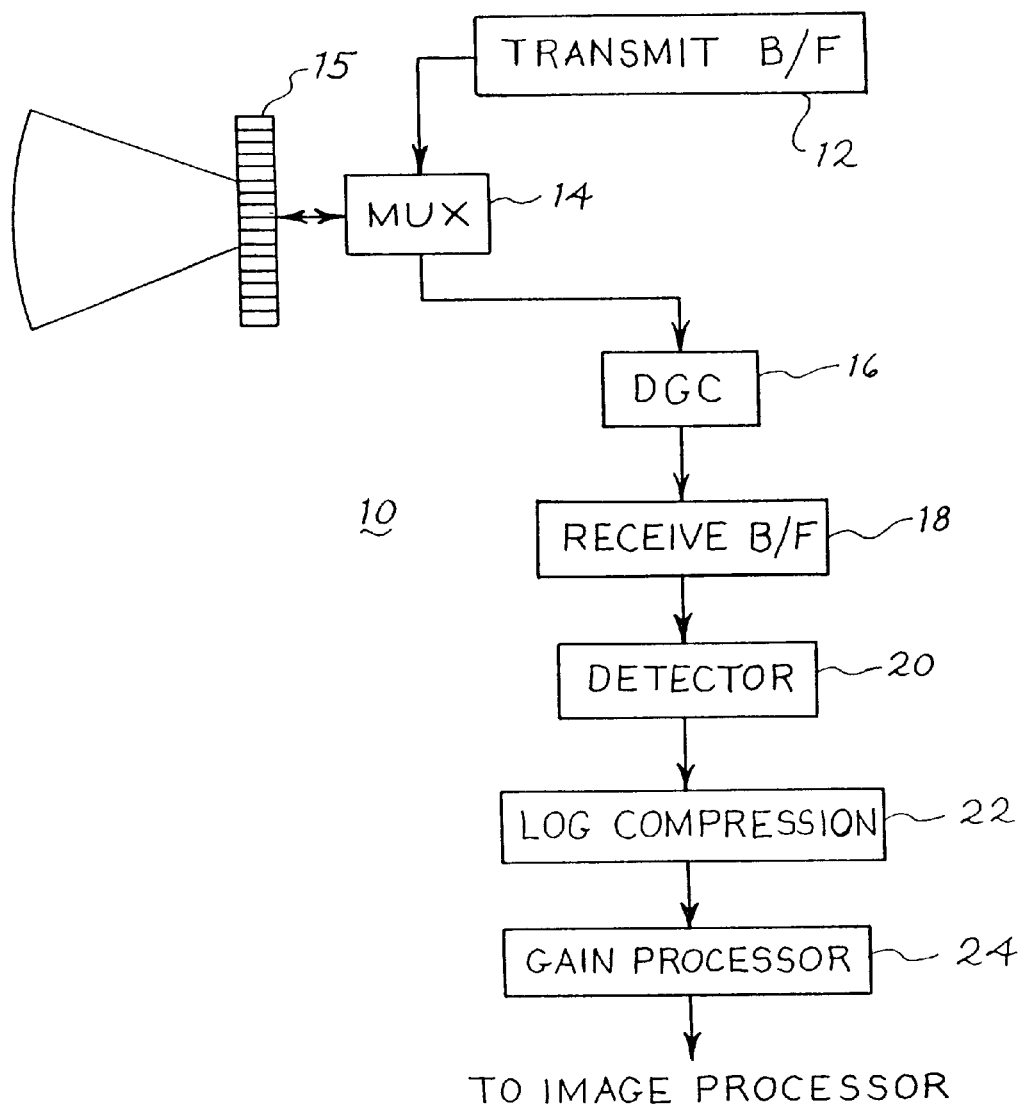
FIG. 1 is a block diagram of a medical diagnostic ultrasonic imaging system that incorporates a presently preferred embodiment of this invention.

Turning now to FIG. 1, an ultrasonic imaging system 10 includes a transmitter such as a transmit beamformer 12 that applies ultrasonic transmit waveforms via a multiplexer 14 to an ultrasonic phased array transducer 15. The transducer 16 forms ultrasonic waves that are transmitted into a region being imaged in a conventional manner.

Returning ultrasonic echoes from the region being imaged are converted into receive signals by the transducer 15. These receive signals are conducted via the multiplexer 14 to a front end amplifier that contains a depth gain compensation circuit 16. The depth gain compensation circuit 16 applies a depth-dependent gain function to the receive signals, as shown for example in FIG. 2. In this way, the gain applied to long range, more-attenuated echo signals is increased as compared to the gain applied to short range, less-attenuated echo signals. The amplified echo signals produced by the depth gain compensation circuit 16 are applied to a receive beamformer 18, which applies controlled delays and phases to cause the echo signals from selected points along selected receive scan lines to be constructively summed. The output of the receive beamformer 18 is applied to a detector 20 and to a log-compression circuit 22.

All the elements 12 to 22 of the system 10 described above can be implemented in any suitable form, using either digital or analog technology. These elements of the system 10 have been provided by way of example in order to provide a framework to allow the preferred embodiments of this invention to be described clearly. It is not intended to limit this invention to any specific form of any of the elements 12 through 22, and many variations are possible. For example, the transmit beamformer 12 and the receive beamformer 18 may be coupled to separate ultrasonic transducers, eliminating the need for a multiplexer 14. A wide variety of transmitters and receivers can be used. The transducer 15 can be 1, 1.5, or 2 dimensional, and mechanical ultrasonic focusing techniques can be used in combination with or in substitution for conventional phased array focusing techniques.

The output signal of the log-compression circuit 22 is applied to a gain processor 24 described in greater detail below. The gain processor 24 selects a gain function for echo signals as described above to improve the SNR for at least some of the signals. The output of the gain processor 24 is applied to a conventional image processor, which may include a scan converter with related buffers and user controls.

Figure 3:
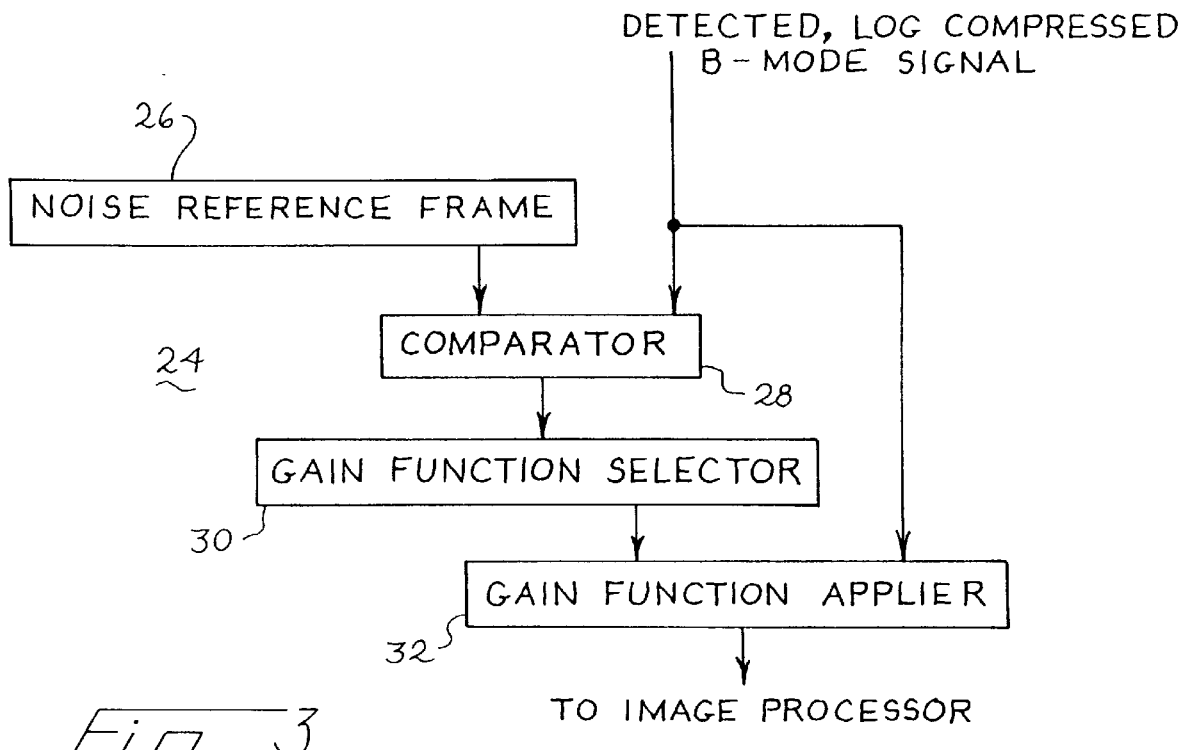
FIG. 3 is a more detailed block diagram of a first embodiment of the gain processor of FIG. 1.

FIG. 3 provides a more detailed block diagram of the gain processor 24. As shown in FIG. 3, both the detected, log-compressed B-mode signal and a noise reference image 26 are applied to a comparator 28. The noise reference image stores a frame of reference values. These reference values may be obtained as described above as a measure of the real time background noise level at a plurality of locations that are preferably varied both in range and in azimuth. As explained above, the reference values may be obtained from a frame of image data acquired without transmitting ultrasonic energy via the transducer 15.

Once the noise reference image has been acquired, the comparator 28 compares detected, log-compressed B-mode image signals on a pixel-by-pixel basis with the corresponding reference values from the noise reference image. Thus, the comparator 28 selects a reference value from the noise reference image at substantially the same range and at substantially the same azimuthal angle for comparison with the B-mode signal. The output of the comparator 28 indicates how much the B-mode signal is greater than or less than the corresponding reference value. The gain function selector 30 then selects a gain in response to the output of the comparator 28. As explained above, the gain function selector may select a gain of unity for those B-mode signals that greatly exceed the reference value of the noise reference image, and the gain function selector may select a gain corresponding to an inverse DGC function for those B-mode signals that are less than the corresponding reference value of the noise reference image.

A smooth gain transition is implemented by the gain function selector when the B-mode signal level is in the vicinity of the noise reference value, using the weighting curve described in FIG. 6. This weighting curve is predetermined and stored in the gain function selector.

A gain function applier 32 receives both the detected, log-compressed B-mode signal and the gain function selected by the gain function selector 30. The gain function applier 32 applies the selected gain function to the B-mode echo signal and outputs the result to the image processor.

Figure 5:
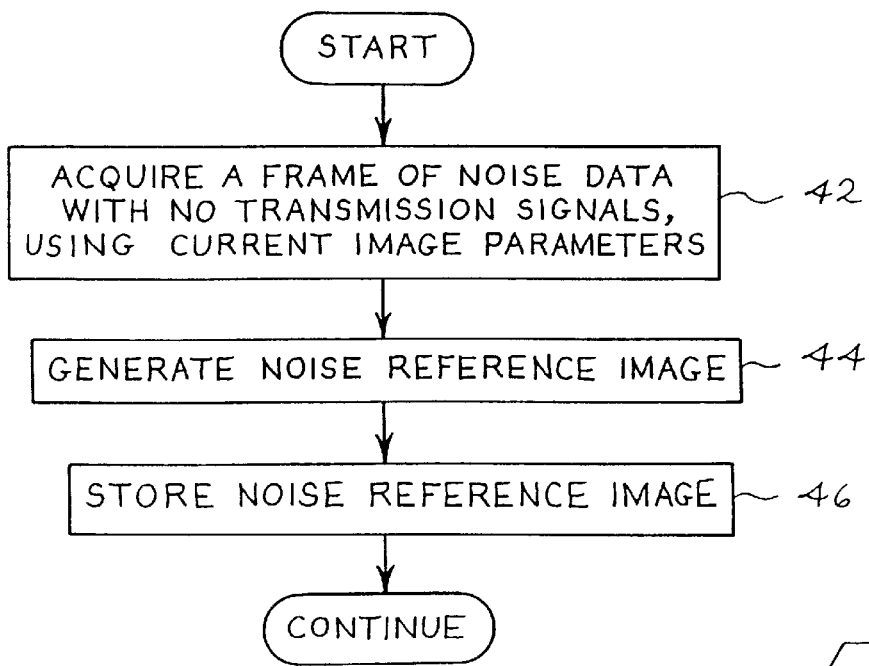
FIG. 5 is a more detailed block diagram of the first step shown in FIG. 4.
Figure 4:
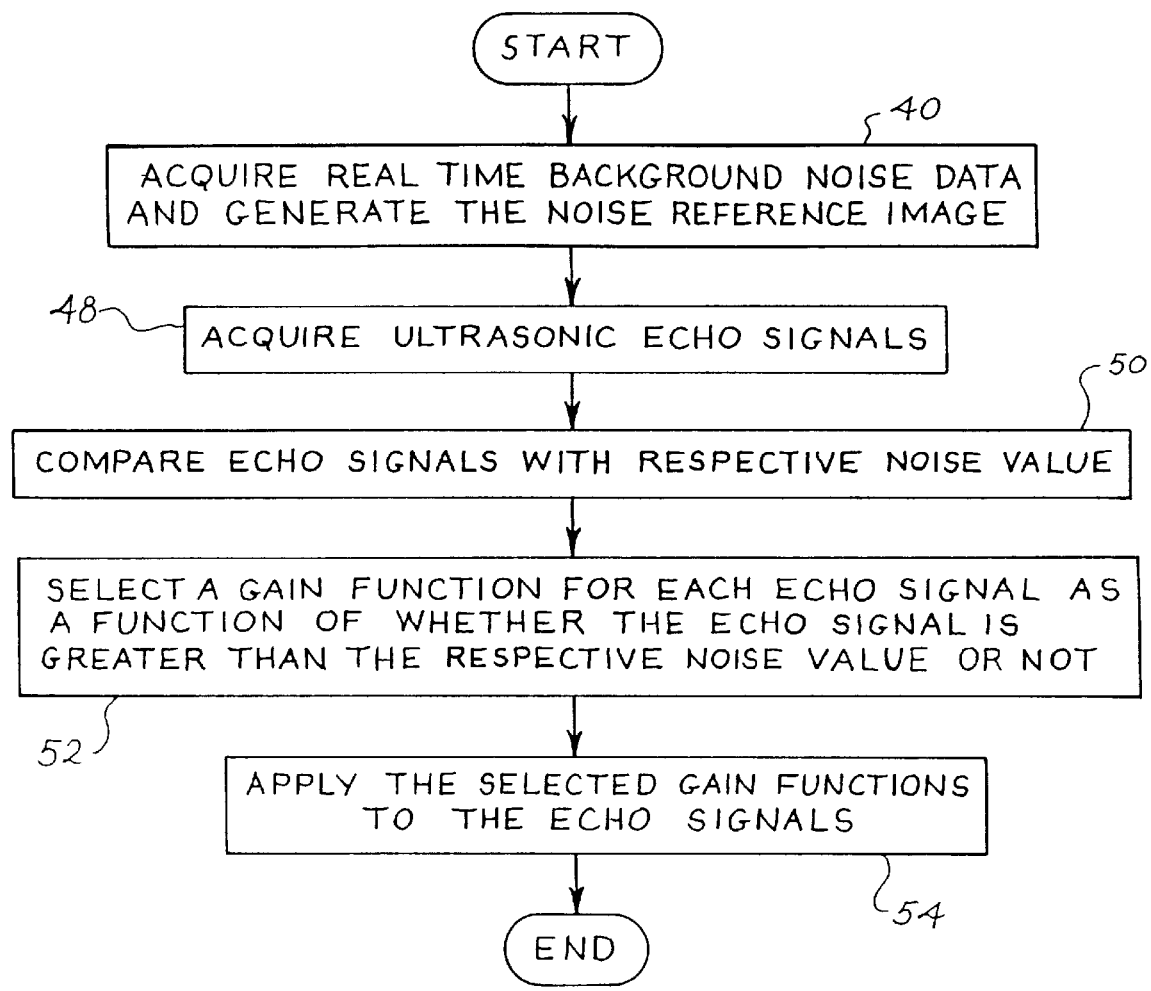
FIG. 4 is a flow chart of an adaptive gain control method practiced by the embodiment of FIG. 1.

FIG. 4 provides a flow chart of the operation of the system 10 using the gain processor 24 described above. First, real time background noise values are obtained by noise frame acquisition in step 40. FIG. 5 shows a detailed block diagram of step 40. The first step 42 of FIG. 5 is to acquire a frame of noise data using no transmission signal and the currently prevailing imaging parameters. Since the acquired noise data is a function of imaging parameters, if the imaging parameters change in the subsequent imaging session, the noise data is preferably re-acquired. Then the reference image is generated from the noise data (step 44) using the methods described above. Then the noise reference image is stored in step 46.

Returning to FIG. 4, the next step in the method is to acquire conventional ultrasonic image or echo signals in step 48. These ultrasonic echo signals have been amplified with a depth-dependent gain compensation applied by the element 16 in the conventional manner, detected and log compressed. Then, in step 50, the acquired echo signals are compared with respective reference values from the noise reference image, and in step 52 a gain function is selected for each echo signal as a function of whether the echo signal is greater than the respective reference value or not.

Finally, in step 54 the selected gain functions are applied to the echo signals before the echo signals are applied to the image processor.

In one embodiment, the gain function selected in step 52 may include unity gain or an inverse DGC gain. When a unity gain is applied to a high SNR echo signal, the depth-dependent gain compensation applied by the element 16 is retained. Conversely, for a low SNR echo signal the inverse DGC function of FIG. 2 is selected, effectively canceling the DGC amplification provided by the element 16 and ensuring that noise (as opposed to signal) is not amplified in an unfavorable way by the system 10.

Figure 7:
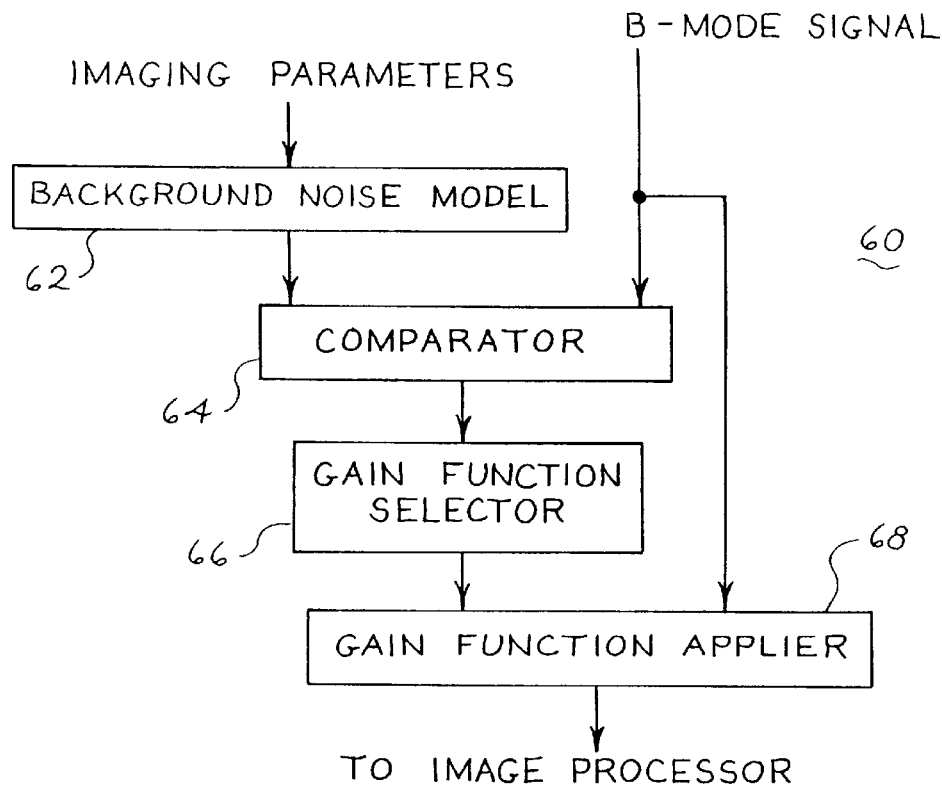
FIG. 7 is a block diagram of an alternative embodiment of the gain processor of FIG. 1.

FIG. 7 shows a block diagram of a gain processor 60 that may be substituted for the gain processor 24 described above. As shown in FIG. 7, the gain processor 60 includes a background noise model 62 that is responsive to the currently prevailing imaging parameters to generate noise reference values indicative of the currently prevailing background noise on a pixel-by-pixel basis. A comparator 64 is responsive to the modeled background noise and to the current B-mode echo signal, and the comparator 64 supplies an output signal indicative of whether the echo signal exceeds the noise reference value. The output of the comparator 64 is applied to a gain function selector 66 that selects the desired gain function in response to the comparison and applies the selected gain function to a gain function applier 68. The gain function applier 68 applies the selected gain function to the B-mode echo signal, and supplies the amplified signal to the image processor.

Figure 8:
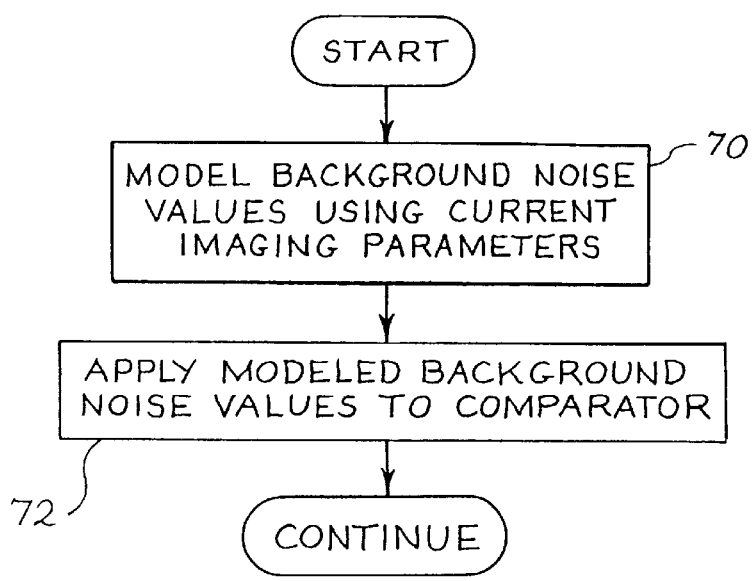
FIG. 8 is a flow chart of an alternative embodiment of the first step shown in FIG. 4.

The method practiced by an imaging system including the gain processor 60 of FIG. 7 is substantially identical to the method flow charted in FIG. 4, except that the first step 40 is preferably implemented as shown in FIG. 8. The first step in FIG. 8 (step 70) is to model the background noise and generate the noise reference image using the currently prevailing imaging parameters. Once this has been done, the method of FIG. 8 then applies the modeled background noise values to the comparator in step 72.

It should be apparent from the foregoing that the embodiments described above apply the conventional DGC function to a B-mode echo signal, but they adaptively change the overall receive signal path gain depending upon the ratio of input signal to background noise. It is anticipated that this non-linear, adaptive gain processing will enhance the output intensity difference between the tissue signal and the background noise. Since the depth gain compensation function is generally an increasing function of depth, the amount of improvement in the ratio of tissue signal to background noise is expected to increase with depth. Thus, noise in the far field will be more suppressed relative to the tissue signal than in the near field, and the perceived penetration should be improved.

Of course, many changes and modifications can be made to the preferred embodiments described above. For example, the adaptive gain control of this invention can be integrated with a front end depth gain compensator. In this alternative, the gain applied by the front end depth gain compensator is made variable, depending upon the SNR comparison.

As an alternative embodiment, the inverse DGC function is synthesized from the acquired noise reference image $I_n^{sm}$ since they are generally proportional. The output image is then formed as $$I_o = I_i - (1-\alpha)I_n^{sm}.$$

In cases where the weighting function $\alpha$ is also a function of $I_i$ and $I_n^{sm}$ the output image $I_o$ can be generalized as $$I_o = F(I_i, I_n^{sm}),$$

which can be implemented using a two-dimensional look-up table acting on samples in either the acoustic or raster domains.

The noise reference image is preferably sufficiently smooth to avoid introducing noise artifacts into the processed image. Two dimensional spatial filtering or temporal filtering can be applied to the acquired noise data $I_n$ to obtain a smooth noise reference image. The noise data can also be acquired at a few selected points in the image and interpolated to create a completely smooth noise reference image with the same grid as the normal image data.

As another embodiment, the input $I_i$ of the weighting function $\alpha$ can be first spatially filtered to make the weighting function smoother. In this case, the weighting function $\alpha x$ is determined as a function of a comparison between the filtered image signal $I_i^{sm}$ and the noise reference image $I_n^{sm}$. This implementation can be mathematically written as $$I_o = I_i - [I - \alpha(I_i^{sm}, I_n^{sm})]I_n^{sm}.$$

Figure 9:
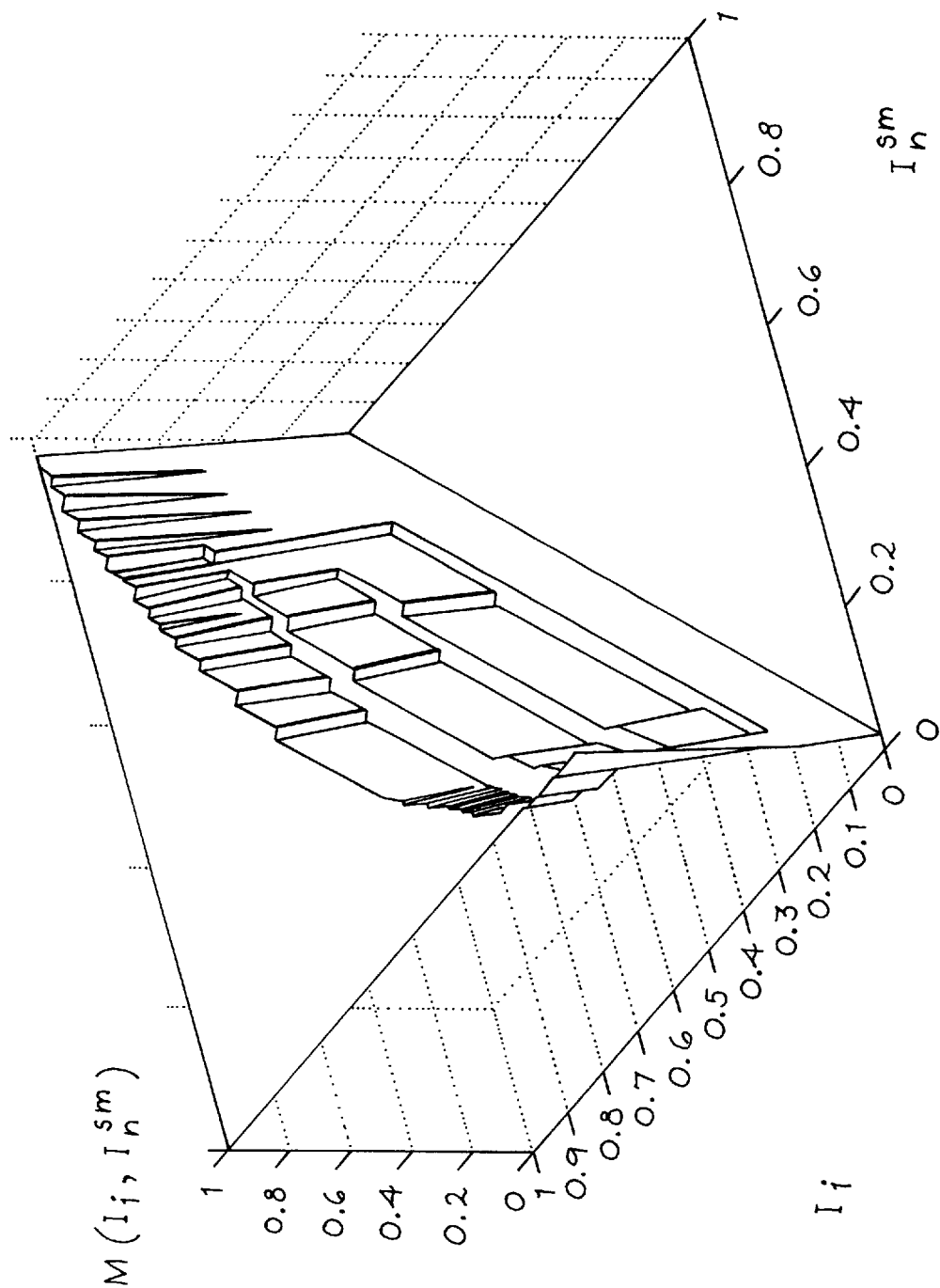
FIG. 9 is a representation of a modulation function suitable for use with this invention.

As another embodiment, the brightness of the original image $I_i$ can be modulated based on a comparison between the original image $I_i$ and the noise reference image $I_n^{sm}$ to produce a final output image $I_o$. This operation can be expressed as $$I_o = I_i M(I_i, I_n^{sm}),$$

where $M(I_i, I_n^{sm})$ is the modulation function. When the image signal at a given pixel is close to or below the noise reference value, the image brightness is preferably reduced by a large amount. When the image signal is well above the noise reference value, then the original image brightness will preferably be left unchanged. When the image signal is near the noise reference value, then the brightness of the original image will be reduced by an amount that varies as a function of the difference between the image signal and the noise reference value. The brightness output can be scaled as a linear or non-linear function of $I_i$ and $I_n^{sm}$. An example of the modulation function M is given in FIG. 9.

In all the examples given above, the original image signal $I_i$ and the acquired noise $I_n$ can be in a number of possible domains in the processing chain (e.g., envelope detected, log-compressed, log-compressed and post processed, processed as described in U.S. Pat. No. 5,479,926 (Ustuner)).

$I_i$ and $I_n$ can be processed in a number of sampling grids (acoustic grid or scan converted grid), and they are not limited in the same sampling grid. As mentioned above, the noise data can be acquired from a more coarsely sampled data set.

Furthermore, though the preferred embodiments described above utilize a two-dimensional frame of noise reference values, the present invention can be implemented in simpler system in which a one-dimensional, range-varying set of reference values is used. For example, the acquired or modeled noise values for the central scan line can be used for both the central scan line of the echo signals as well as other scan lines of the echo signals.

The gain processors 24, 60 are conveniently implemented with any suitable digital computer system programmed for digital storage, calculation and comparison as described above, though any suitable implementation can be used. For example, analog circuits can also be adapted to perform the functions described above.

As used herein, the term "function of" is intended broadly to encompass linear and non-linear functions, including functions quite different from those described by way of illustration above.

The step of comparing is intended broadly to encompass both ratio comparisons and threshold comparisons. By way of example, the comparing step can be performed by comparing the ratio of the echo signal to background noise reference to a threshold, or by comparing the difference between the echo signal and the background noise reference to a threshold.

The term "depth-dependent gain function" is intended broadly to encompass gain functions that vary both directly and inversely with depth or range. The term "real time background noise" is intended to encompass background noise acquired or modeled within the same imaging session during which the imaging parameters are not varied.

The term "imaging parameter" is intended to encompass any parameter that may affect the background noise of the image, including imaging frequency, transmit focus, dynamic range, and the size of imaging field of view, by way of example.

The term "response function" is intended broadly to encompass any function that relates an input signal to an output signal. Thus, examples of response functions include all of the gain functions and modulation functions discussed above. Response functions can be implemented in many ways, including look up tables, amplifiers and computational algorithms.

The foregoing detailed description has discussed only a few of the many forms that the present invention can take.

For this reason, this invention is intended by way of illustration and not by way of limitation. It is only the following claims, including all equivalents, that are intended to define the scope of this invention.

What is claimed is:

1. In a diagnostic medical ultrasonic imaging system, a method for controlling receive signal response comprising:
   (a) storing a plurality of reference values indicative of acquired real time background noise at a respective plurality of locations within an image frame;
   (b) at the plurality of locations selecting respective response functions in response to at least one respective ultrasonic echo signal and at least one respective reference value; and
   (c) applying the selected response functions to the respective ultrasonic echo signals.

2. In a diagnostic medical ultrasonic imaging system, a method for controlling receive signal response comprising:
   (a) modeling a plurality of reference values indicative of background noise at a respective plurality of locations within an image frame as a function of currently prevailing imaging parameters;
   (b) at the plurality of locations selecting respective response functions in response to at least one respective ultrasonic echo signal and at least one respective reference value; and
   (c) applying the selected response functions to the respective ultrasonic echo signals.

3. The method of claims 1 or 2 wherein the ultrasonic echo signals comprise B-mode echo signals.

4. The method of claims 1 or 2 wherein the response functions comprise depth-dependent response functions.

5. The method of claims 1 or 2 wherein the plurality of locations comprise range varying locations.

6. The method of claims 1 or 2 wherein the plurality of locations vary in range and azimuth.

7. The method of claim 1 wherein the reference values of (a) vary as a smoothing function of acquired real time background noise.

8. The method of claim 7 wherein the plurality of locations are distributed over at least two spatial dimensions.

9. The method of claims 1 or 2 wherein the response functions of (b) additionally vary as a function of a weighting function.

10. The method of claim 9 wherein the plurality of locations are distributed over at least two spatial dimensions.

11. The method of claim 9 wherein the weighting function varies as a smoothing function of the ultrasonic echo signals.

12. The method of claim 11 wherein the plurality of locations are distributed over at least two spatial dimensions.

13. The method of claim 1 wherein the response functions of (b) comprise gain functions.

14. The method of claim 1 wherein the response functions of (b) comprise modulation functions.

15. The method of claim 2 wherein the plurality of locations are distributed over at least two spatial dimensions.

16. The method of claims 1 or 2 wherein (b) comprises:
   (b1) comparing the ultrasonic echo signal associated with each of the locations with the respective reference value associated with the same one of the locations; and
   (b2) selecting the respective response function as a function of the comparing of (b1).

17. The method of claim 16 wherein the plurality of locations are distributed over at least two spatial dimensions.

18. In a diagnostic medical ultrasonic imaging system, a receive signal response processor comprising:

means for storing a plurality of reference values indicative of acquired real time background noise at a respective plurality of locations within an image frame;

means for selecting at a plurality of locations respective response functions in response to at least one respective ultrasonic echo signal and at least one respective reference value; and means for applying the selected response functions to the respective ultrasonic echo signals.

19. In a diagnostic medical ultrasonic imaging system, a receive signal response processor comprising:

means for modeling a plurality of reference values indicative of background noise at a respective plurality of locations within an image frame as a function of currently prevailing imaging parameters;

means for selecting at the plurality of locations respective response functions in response to at least one respective ultrasonic echo signal and at least one respective reference value; and means for applying the selected response functions to the respective ultrasonic echo signals.

20. The invention of claims 18 or 19 wherein the ultrasonic echo signals comprise B-mode echo signals.

21. The invention of claims 18 or 19 wherein the response functions comprise depth-dependent response functions.

22. The invention of claims 18 or 19 wherein the plurality of locations comprise range varying locations.

23. The invention of claims 18 or 19 wherein the plurality of locations vary in range and azimuth.

24. The invention of claim 18 wherein the storing means causes the reference values to vary as a smoothing function of acquired real time background noise.

25. The invention of claim 24 wherein the plurality of locations are distributed over at least two spatial dimensions.

26. The invention of claims 18 or 19 wherein the selecting means selects the response functions as an additional function of a weighting function.

27. The invention of claim 26 wherein the plurality of locations are distributed over at least two spatial dimensions.

28. The invention of claim 26 wherein the weighting function varies as a smoothing function of the ultrasonic echo signals.

29. The invention of claim 28 wherein the plurality of locations are distributed over at least two spatial dimensions.

30. The invention of claims 18 or 19 wherein the response functions comprise gain functions.

31. The invention of claims 18 or 19 wherein the response functions comprise modulation functions.

32. The invention of claims 18 or 19 wherein the plurality of locations are distributed over at least two spatial dimensions.

33. The invention of claims 18 or 19 wherein the selecting means comprises:

means for comparing the ultrasonic echo signal associated with each of the locations with the respective reference value associated with the same one of the locations; and means for selecting the respective response function in response to the comparing means.

34. The invention of claim 33 wherein the plurality of locations are distributed over at least two spatial dimensions.

* * * * *

UNITED STATES PATENT AND TRADEMARK OFFICE
CERTIFICATE OF CORRECTION

PATENT NO.        : 6,120,446           Page 1 of 2
APPLICATION NO. : 09/213666
DATED             : September 19, 2000
INVENTOR(S)      : Ting-Lan Ji et al.

It is certified that error appears in the above-identified patent and that said Letters Patent is hereby corrected as shown below:

On the Title Page

In column 2, after line 6, insert:

--5,735,797     4/1998        Muzilla et al.        600/441--.

In column 2, after line 7, insert:

--5,933,392     11/1992       Roundhill et al.      600/447--.

In the Specification

In column 3, line 7, delete "(X, Y)" and substitute --(x, y)-- in its place.

In column 3, line 22, delete "ox" and substitute --α-- in its place.

In column 3, line 45, after "(r)" insert --)-- (parenthesis).

In column 6, line 38, delete "αis" and substitute --α is-- in its place.

In column 6, line 56, delete "ax" and substitute --α-- in its place.

In the Claims

Col. 8 in Claim 3, line 1, delete "claims" and substitute --claim-- in its place.

Col. 8 in Claim 4, line 1, delete "claims" and substitute --claim-- in its place.

Col. 8 in Claim 5, line 1, delete "claims" and substitute --claim-- in its place.

Col. 8 in Claim 6, line 1, delete "claims" and substitute --claim-- in its place.

Col. 8 in Claim 9, line 1, delete "claims" and substitute --claim-- in its place.

Col. 8 in Claim 15, line 1, delete "claim 2" and substitute --claim 1 or 2-- in its place.

Col. 8 in Claim 16, line 1, delete "claims" and substitute --claim-- in its place.

UNITED STATES PATENT AND TRADEMARK OFFICE
CERTIFICATE OF CORRECTION

PATENT NO. : 6,120,446
APPLICATION NO. : 09/213666
DATED : September 19, 2000
INVENTOR(S) : Ting-Lan Ji et al.

It is certified that error appears in the above-identified patent and that said Letters Patent is hereby corrected as shown below:

Col. 9 in Claim 20, line 1, delete "claims" and substitute --claim-- in its place.

Col. 9 in Claim 21, line 1, delete "claims" and substitute --claim-- in its place.

Col. 9 in Claim 22, line 1, delete "claims" and substitute --claim-- in its place.

Col. 9 in Claim 23, line 1, delete "claims" and substitute --claim-- in its place.

Col. 10 in Claim 26, line 1, delete "claims" and substitute --claim-- in its place.

Col. 10 in Claim 30, line 1, delete "claims" and substitute --claim-- in its place.

Col. 10 in Claim 31, line 1, delete "claims" and substitute --claim-- in its place.

Col. 10 in Claim 32, line 1, delete "claims" and substitute --claim-- in its place.

Col. 10 in Claim 33, line 1, delete "claims" and substitute --claim-- in its place.

Signed and Sealed this

Nineteenth Day of February, 2008

JON W. DUDAS
*Director of the United States Patent and Trademark Office*